United States Patent
Kumar et al.

(10) Patent No.: US 9,481,876 B2
(45) Date of Patent: Nov. 1, 2016

(54) CATHEPSIN L INHIBITORS AND PROBES COMPRISING VINYL SULFONATE MOIETY AND METHODS OF USING SAME

(71) Applicant: Research Foundation of the City University of New York, New York, NY (US)

(72) Inventors: Sanjai Kumar, Oceanside, NY (US); Dibyendu Dana, Flushing, NY (US)

(73) Assignee: Research Foundation of the City University of New York, New York, NY (US)

( * ) Notice: Subject to any disclaimer, the term of this patent is extended or adjusted under 35 U.S.C. 154(b) by 18 days.

(21) Appl. No.: 14/721,513

(22) Filed: May 26, 2015

(65) Prior Publication Data

US 2015/0337286 A1   Nov. 26, 2015

Related U.S. Application Data

(60) Provisional application No. 62/002,223, filed on May 23, 2014.

(51) Int. Cl.
*C12N 9/64*     (2006.01)
*C07C 309/69*   (2006.01)

(52) U.S. Cl.
CPC ........... *C12N 9/6472* (2013.01); *C07C 309/69* (2013.01); *C07B 2200/07* (2013.01); *C12Y 304/22015* (2013.01)

(58) Field of Classification Search
USPC ...................................................... 514/709
See application file for complete search history.

(56) References Cited

PUBLICATIONS

Brinen (A target within the target: proving cruzain's P1' site to define structural determinants for the Chagas' disease protease, Department of Pathology, University of California, San Francisco, San Francisco, CA, 94143, USA, Structure (London) (2000), 8(8), 831-840).*
Dana, Dibyedu et al.; Development of a highly potent, selective, and cell-active Inhibitor of cysteine cathepsin L—A hybrid design approach; ChemComm Communication; Aug. 24, 2014; pp. 10875-10878; vol. 50; The Royal Society of Chemistry 2014; US.
Roush, William R. et al.: Vinyl Sulfonate Esters and Vinyl Sulfonamides:Potent, Irreversible Inhibitors of Cysteine Proteases; J. Am. Chem. Soc.; Oct. 10, 1998; pp. 10994-10995; vol. 120; American Chemical Society; US.
Powers, James C. et al.; Irreversible Inhibitors of Serine, Cysteine, and Threonine Proteases; Chem. Rev.; Nov. 8, 2002; pp. 4639-4750; vol. 102; American Chemical Society; US.
Torkar, Ana et al.; A Novel Photoaffinity-Based Probe for Selective Detection of Cathepsin L Active Form; ChemBioChem 2012, Nov. 24, 2012; pp. 2616-2621; vol. 13; Wiley-VCH Verlag GmbH& Co. KGaA, Weinheim.
Fonovic, Marko et al.; Activity Based Probes for Proteases: Applications to Biomarker Discovery, Molecular Imaging and Drug Screening; Current Pharmaceutical Design, Jan. 2007; pp. 253-261; vol. 13; Bentham Science Publishers Ltd.; US.
Nomura, Daniel K. et al.; Activity-based protein profiling for biochemical pathway discovery in cancer; Focus on Cancer Proteomics; Aug. 12, 2010; pp. 630-638; vol. 10; Macmillan Publishers Limited.; US.
Leto, Gaetano et al.; Cathepsin L in metastatic bone disease: therapeutic implications; Biological Chemistry; Apr. 6, 2010; pp. 655-664; vol. 391; Walter de Gruyter; US.
Joyce, Johanna A. et al.; Cathepsin cysteine proteases are effectors of invasive growth and angiogenesis during multistage tumorigenesis; Cancer Cell; May 2004; pp. 443-453; vol. 5; Cell Press; US.
Zajc, Irena; et al.; Cathepsin L Affects Apoptosis of Glioblastoma Cells:a Potential Implication in the Design of Cancer Therapeutics; Anticancer Research; 2006; pp. 3357-3364; 26; Anticancer Research; Slovenia.
Nakagawa, Terry et al.; Cathepsin L: Critical Role in Ii Degradation and CD4 T Cell Selection in the Thymus; Science; Apr. 17, 1998; pp. 450-453; vol. 280; American Association for the Advancement of Science; US.
Yasothornsrikul; Sukkid et al.; Cathepsin L in secretory vesicles functions as a prohormone-processing enzyme for production of the enkephalin peptide neurotransmitter; PNAS; Aug. 5, 2003; pp. 9590-9595; vol. 100, No. 16; US.
Gocheva, Vasilena et al.; Cysteine Cathepsins and the Cutting Edge of Cancer Invasion; Cell Cycle; Jan. 15, 2007; vol. 6 Issue 1; pp. 60-64; Landes Bioscience; US.
Turk, Vito et al.; Cysteine cathepsins: From structure, function and regulation to new frontiers; Biochimica et Biophysica Acta; Oct. 12, 2011; pp. 68-88; Elsevier B.V.; Slovenia.
Mohamed, Mona Mostafa et al.; Cysteine cathepsins: multifunctional enzymes in cancer; Tumour Microenvironment; Oct. 2006; pp. 764-775; vol. 6.; Nature Publishing Group; US.
Skrzypczak, Maciej et al.; Expression of Cysteine Protease Cathepsin L is Increased in Endometrial Cancer and Correlates With Expression of Growth Regulatory Genes; Cancer Investigation; Mar. 27, 2012; pp. 398-403; vol. 30; Informa Healthcare USA, Inc.; US.

(Continued)

*Primary Examiner* — Kathrien Cruz
(74) *Attorney, Agent, or Firm* — Peter J. Mikesell; Schmeiser, Olsen & Watts, LLP

(57) ABSTRACT

Human cathepsin L inhibitors and probes containing a vinyl sulfonate ester moiety are described. The inhibitors are highly potent (low nM affinity), selective, and cell permeable, and can inhibit ultra-low concentration of active cathepsin L. The developed probes are highly sensitive and can detect an ultra-low amount of probe-labeled active cathespin L.

20 Claims, 10 Drawing Sheets

(56) References Cited

PUBLICATIONS

Torkar, Ana et al.; Identification of new peptide amides as selective cathepsin L inhibitors: The firststep towards selective irreversible inhibitors?; Bioorganic &Medicinal Chemistry Letters; Mar. 20, 2013; pp. 2968-2973; vol. 23; Elsevier Ltd. Slovenia.

Verdoes, Martijn et al; Improved Quenched Fluorescent Probe for Imaging of Cysteine Cathepsin Activity; Journal of the American Chemical Society; Aug. 23, 2013; pp. 14726-14730; vol. 135; American Chemical Society; US.

Zhang, Wei et al.; Overexpression of cysteine cathepsin L is a marker of invasion and metastasis in ovarian cancer; Oncology Reports; Jan. 8, 2014; pp. 1334-1342; vol. 31; Spandidos Publications.

Roush, William R. et al.; Potent Second Generation Vinyl Sulfonamide Inhibitors of the Trypanosomal Cysteine Protease Cruzain; Bioorganic& Medicinal Chemistry Letters; Oct. 22, 2001; pp. 2759-2762; vol. 11; Elsevier Science Ltd; US.

Rawlings, Neil D. et al.; MEROPS: the database of proteolytic enzymes, their substrates and inhibitors; Nucleic Acids Research; Nov. 15, 2011; pp. D343-D350; vol. 40; Oxford University Press; UK.

Palmer, James T. et al; Vinyl Sulfones as Mechanism-Based Cysteine Protease Inhibitors; Journal of Medicinal Chemistry; Aug. 1995; pp. 3193-3196; vol. 38; American Chemical Society; US.

* cited by examiner

FIG. 3B

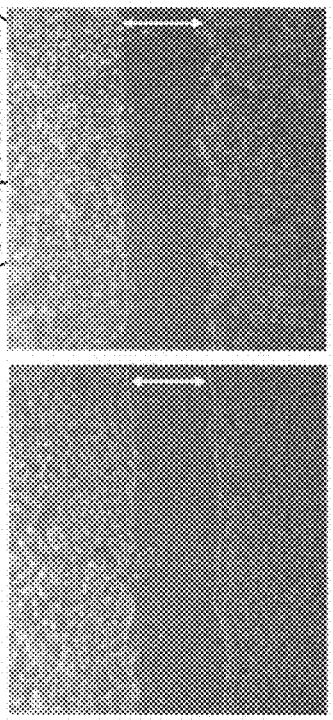
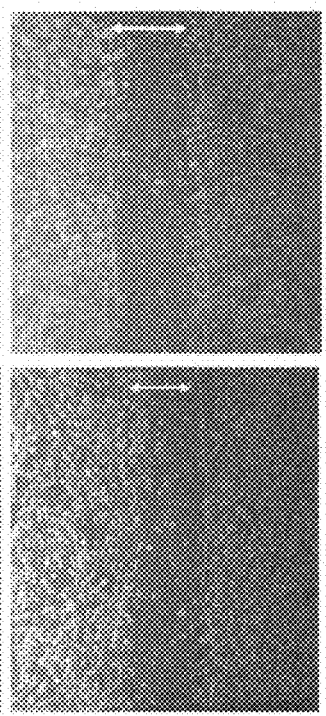
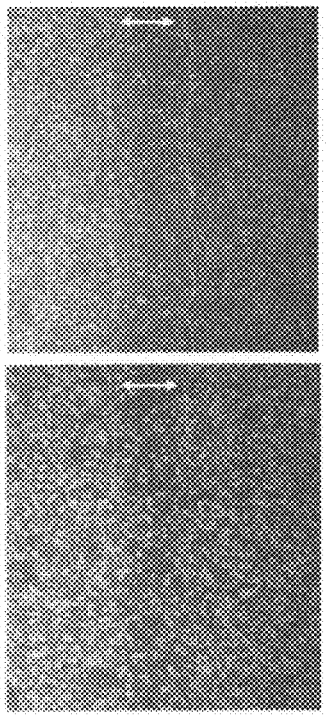
FIG. 6A t = 0 hr
FIG. 6B t = 7 hrs
FIG. 6C t = 22 hrs
FIG. 6D
FIG. 6E
FIG. 6F

CATHEPSIN L INHIBITORS AND PROBES COMPRISING VINYL SULFONATE MOIETY AND METHODS OF USING SAME

CROSS-REFERENCE TO RELATED APPLICATIONS

This application claims priority to and is a non-provisional of U.S. Patent Application Ser. No. 62/002,223 (filed May 23, 2014) the entirety of which is incorporated herein by reference.

BACKGROUND OF THE INVENTION

The subject matter disclosed herein relates to inhibitors of cysteine cathepsins. Cysteine cathepsins are an important family of enzymes that are implicated in a variety of human diseases. Consequently they are considered key therapeutic targets for drug development. Cathepsin L is an important member of this family which is found to be overexpressed in a variety of human cancer and osteoporosis. Aberrant expression and activation of cathepsin L has been implicated in many forms of human diseases. These include highly invasive cancer, cardiovascular, lung, immune, and metabolic disorders. Cathepsin L is notably overabundant in a variety of metastatic cancer cells, including cancers from glial, breast, melanoma, and myeloma origins. In glial cells, Cathepsin L overexpression can lead to progression from astrocytoma to high-grade malignant glioblastoma, a most deadly form of brain tumor. Importantly, selective inhibition of cathepsin L abrogates human brain cell invasion, and promotes apoptosis. Cathepsin L can promote metastatic behavior by efficiently degrading and hydrolyzing various components of extracellular matrix (ECM), such as laminin, fibronectin, and collagen IV. These studies strongly indicate that cathepsin L could activate signaling pathways relevant to invasion in metastatic cancer. Inhibitory perturbation in highly invasive cancer types is therefore considered an attractive strategy for anti-cancer drug development. Thus, inhibition of cathepsin L with suitable small molecule inhibitors is desired for development of suitable chemotherapeutic agents. There is also a significant gap in understanding cathepsin L biology. Potent, selective, and cell permeable small molecule inhibitors, and probes are desired so they can be utilized to understand the undocumented function of this important enzyme. Unfortunately, highly selective, potent and cell permeable inhibitors and probes remain scarcely available for cathepsin L.

The discussion above is merely provided for general background information and is not intended to be used as an aid in determining the scope of the claimed subject matter.

BRIEF DESCRIPTION OF THE INVENTION

Human cathepsin L inhibitors and probes containing a vinyl sulfonate ester moiety are described. The inhibitors are highly potent (low nM affinity), selective, and cell permeable, and can inhibit ultra-low concentration of active cathepsin L. The developed probes are highly sensitive and can detect an ultra-low amount of probe-labeled active cathespin L.

In a first embodiment, a method for inhibiting cathepsin L or probing the activity of cathepsin L is provided. The method comprises exposing a biological cell to a compound of Formula (A) or a pharmaceutically acceptable solvate, hydrate, salt or N-oxide thereof. Formula (A) is given by:

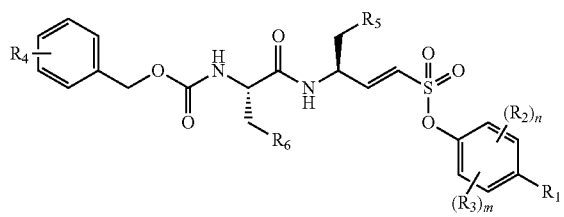

wherein $R_1$ is selected from the group consisting of Br, Cl, I, an aryl, $CO_2CH_3$, CN and $NO_2$; each $R_2$ is independently selected from the group consisting of F, $CF_3$, aryl and methyl; each $R_3$ is independently selected from the group consisting of F, $CF_3$ aryl and methyl; $R_4$ is selected from the group consisting of H, CCH and $N_3$; $R_5$ is selected from the group consisting of methyl, ethyl and propyl; $R_6$ is an aryl; n is 0, 1 or 2 and m is 0, 1 or 2.

In a second embodiment, a composition of matter is provided. The composition of matter comprises a structure given by Formula (A) or a pharmaceutically acceptable solvate, hydrate, salt or N-oxide thereof. Formula (A) is given by:

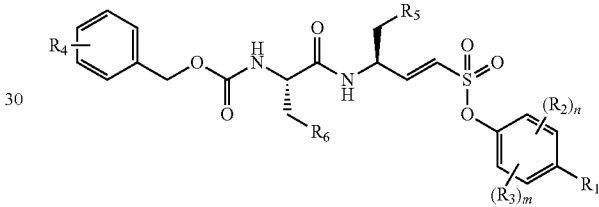

wherein, $R_1$ is selected from the group consisting of Br, Cl, I, an aryl, $CO_2CH_3$, CN and $NO_2$; each $R_2$ is independently selected from the group consisting of F, $CF_3$, aryl and methyl; each $R_3$ is independently selected from the group consisting of F, $CF_3$ aryl and methyl; $R_4$ is selected from the group consisting of H, CCH and $N_3$; $R_5$ is selected from the group consisting of methyl, ethyl and propyl; $R_6$ is an aryl; n is 0, 1 or 2 and m is 0, 1 or 2.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which:

FIG. 3A and FIG. 3B are depictions of a library of precursors for constructing various cathepsin L inhibitors;

FIG. 6A, FIG. 6B and FIG. 6C are micrographs of control cells (DMSO-treated) showing bright field images at various time intervals in wound-healing assay;

FIG. 6D, FIG. 6E and FIG. 6F are micrographs of a cells exposed to a cathepsin L inhibitor showing bright field images at various time intervals of inhibitor treatment in wound-healing assay;

DETAILED DESCRIPTION OF THE INVENTION

Figure 1:
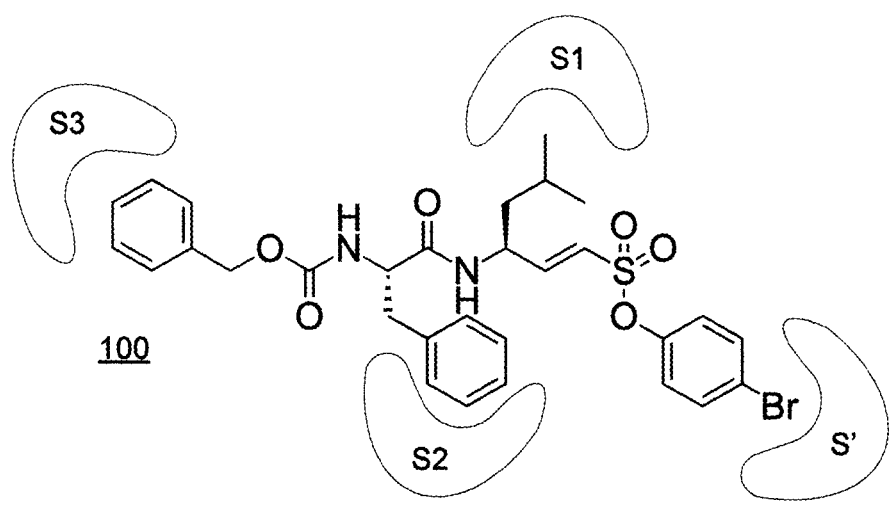
FIG. 1 is depiction of an exemplary cathepsin L inhibitor.

Disclosed in this specification are cathepsin L-specific inhibitors that provide non-basic small molecules to reduce or block human cathepsin L activity in intact cells. The disclosed human cathepsin L inhibitors are the first of their kind and exploit a vinyl sulfonate-based moiety to inhibit cathepsin L activity. See, for example, compound 100 in FIG. 1.

Without wishing to be bound to any particular theory, an inhibitor agent that includes a vinyl sulfonate ester moiety and also contains groups that target both prime (S') and non-prime site (S1, S2, and S3) residues of cathepsin L is believed to provide an effective strategy for developing highly potent and selective inhibitory agent.

Figure 2:
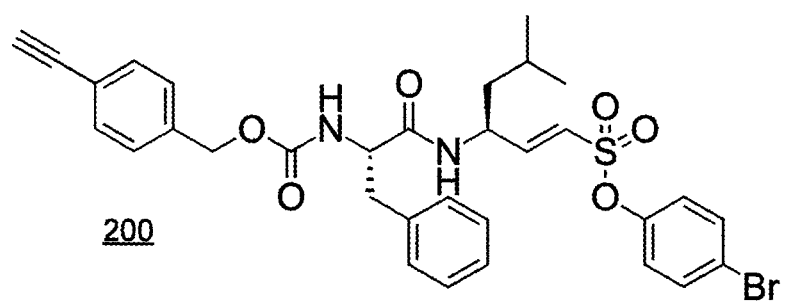
FIG. 2 is a depiction of an exemplary cathepsin L probe.

Also disclosed in this specification are activity-based probes of cathepsin L. Activity-based cathepsin L probes (see, for example, compound 200, FIG. 2) find extensive use in a variety of research applications, relevant to cathepsin-based anti-cancer drug development endeavors. These, for instance, include (a) using in situ tumor models for probing cathepsin L function, (b) validation of cathepsin L as a viable therapeutic target in individual cancer types, (c) assessment of in vivo pharmacodynamics property and efficacy of drug candidates, and (d) estimation of drug's selectivity and off-target reactivity, (e) investigating the importance of targeting cathepsin L alone in cancer cells (or any diseased cells) that overexpress both cathepsin L and cathepsin B; this is especially important given the fact these two share a common physiological protein substrate of extracellular matrix, a protein known to promote metastasis, and (f) profiling the selectivity of cathepsin L-directed anti-cancer drug candidates in vivo.

A hybrid ligand was designed that included (a) the prime site-targeting vinyl sulfonate ester, and (b) chemical groups that target regular non-prime sites (S1, S2 and S3) for suitable binding interactions. Chemical functional groups that were basic in nature were precluded to ensure that the developed inhibitory compounds do not accumulate in the acidic environment of lysosome.

Figure 3A:
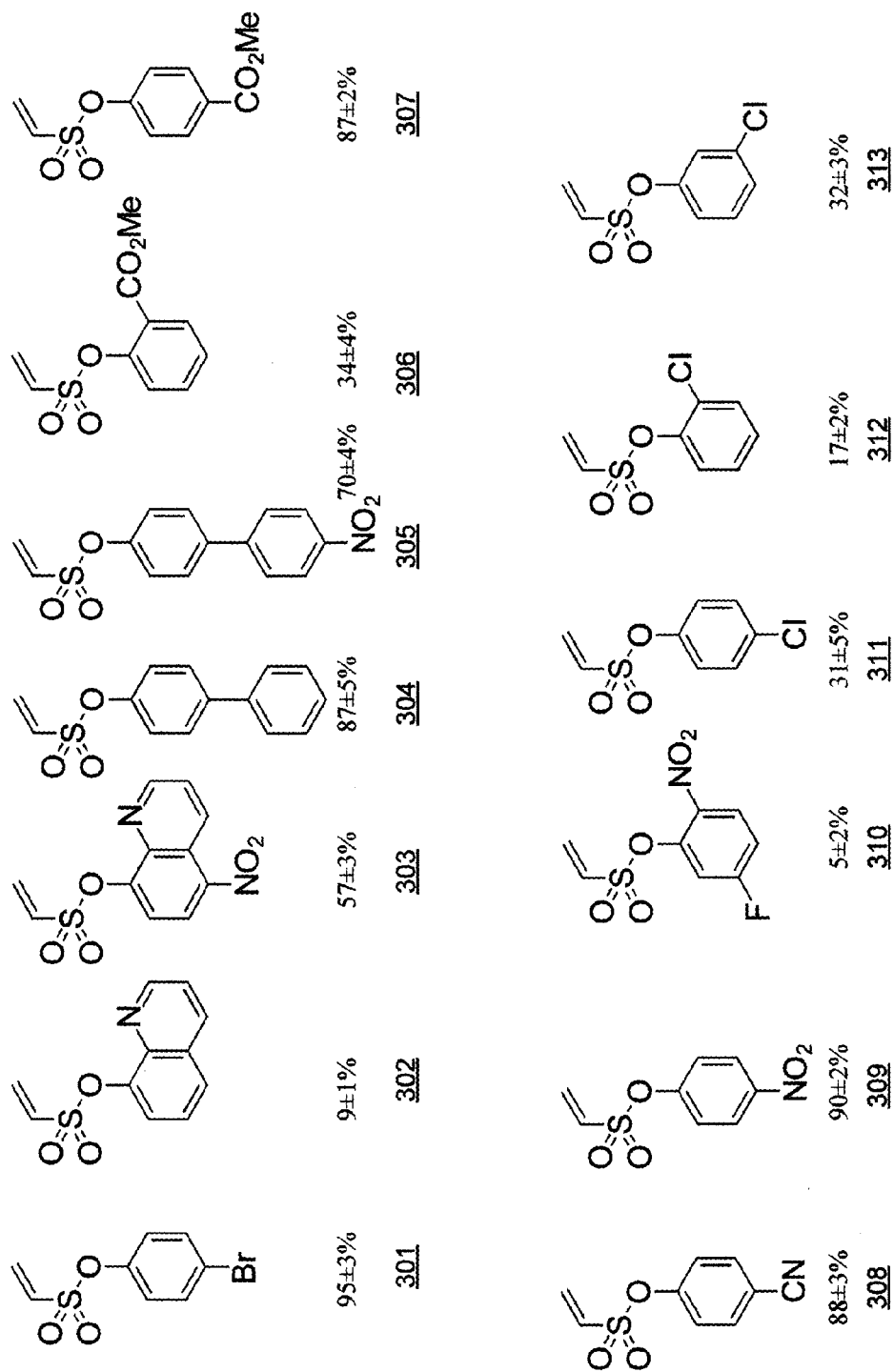
Figure 3B:
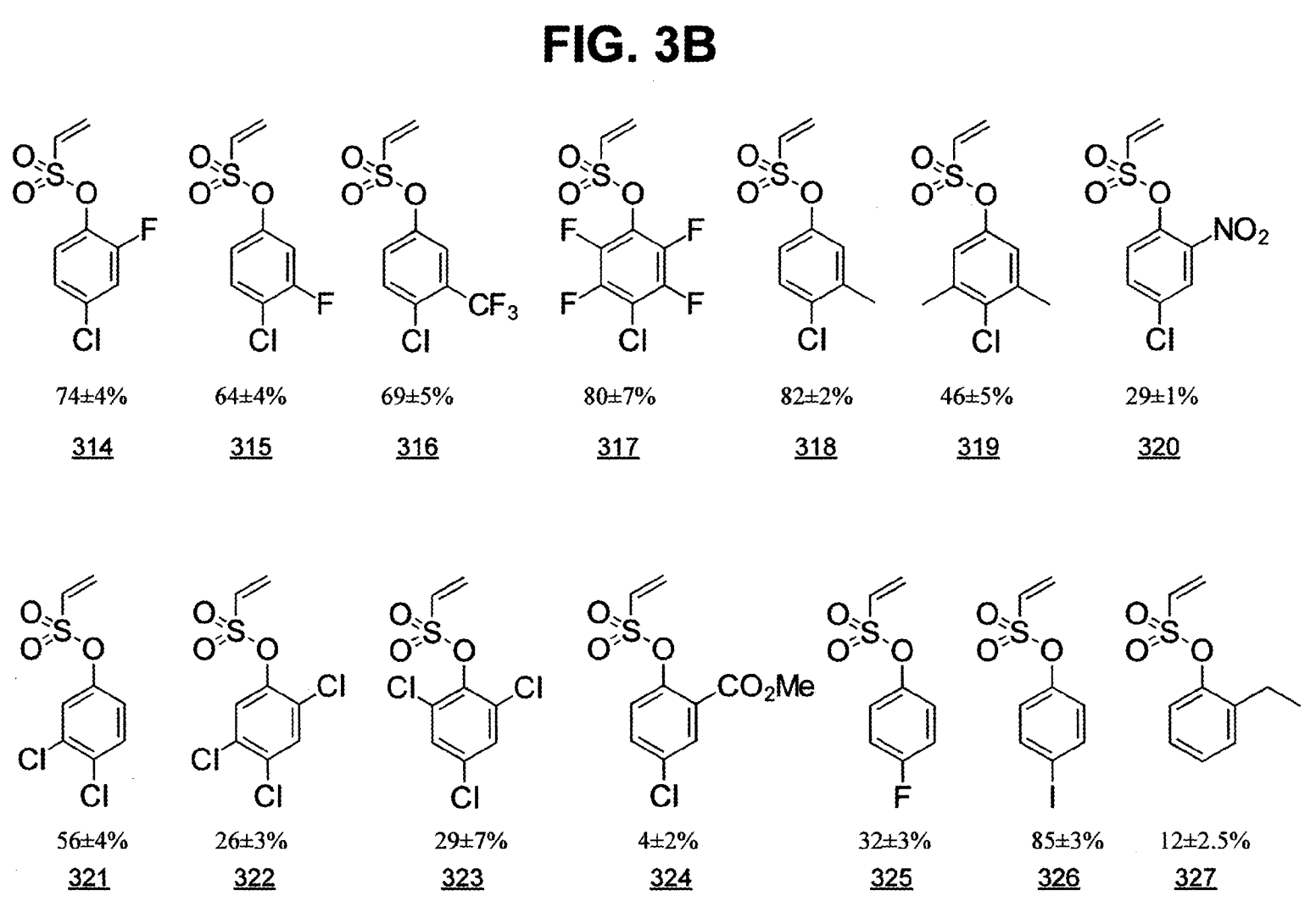

An initial inhibitory screen of various precursors (see FIG. 3A and FIG. 3B) was performed at 10 µM against recombinant human cathepsin L. The percent inhibition of each precursor is shown below its corresponding precursor in FIG. 3A and FIG. 3B. Precursor 301 was identified as a lead precursor with a 95±3% inhibition. In some embodiments, one or more of the 2, 3, 5 and/or 6 positions are occupied by an aryl group. Examples of suitable aryl groups include NHPh, OPh or homologs thereof.

Figure 4A:
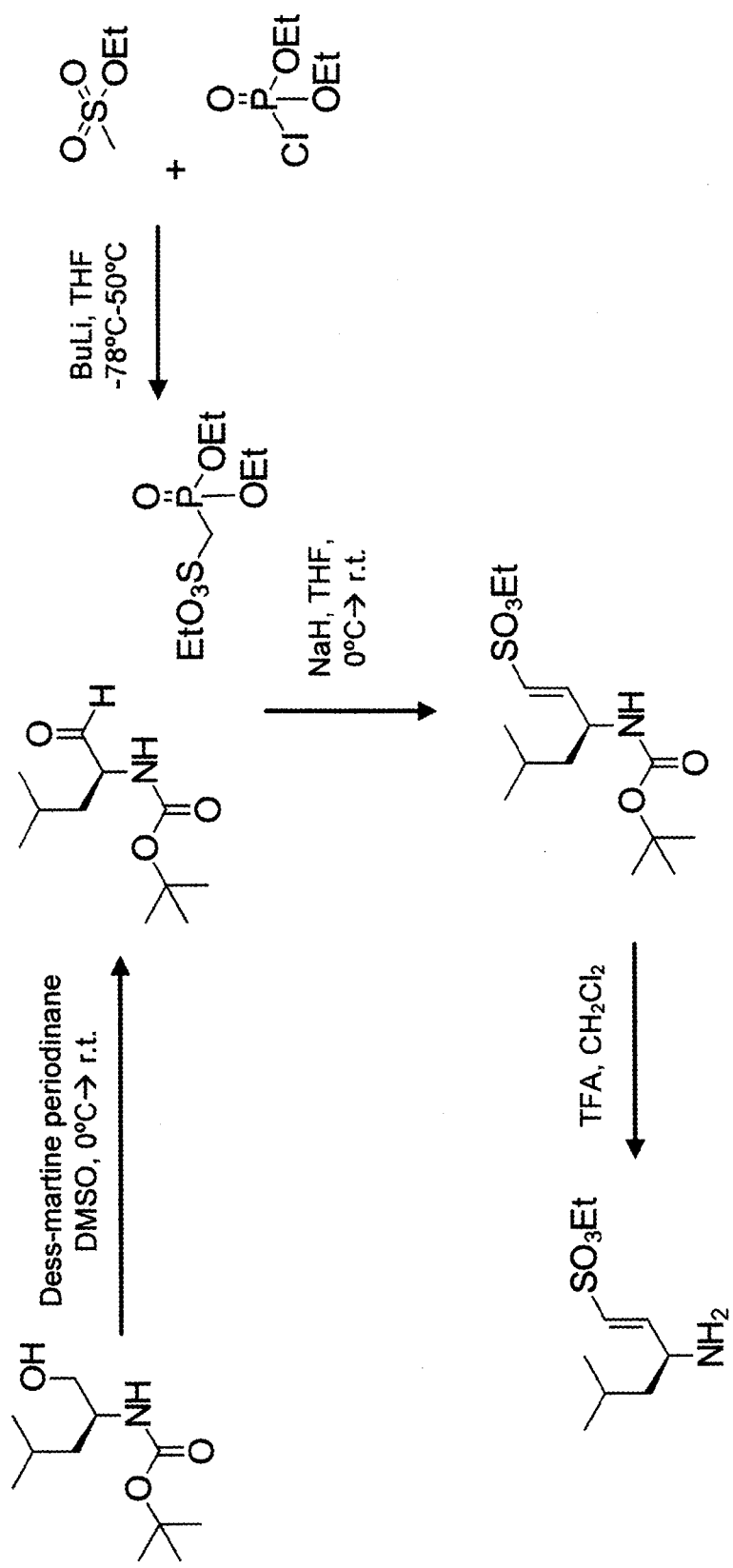
FIG. 4A is a synthetic scheme for preparing a vinyl sulfonate intermediate for use in constructing cathepsin L inhibitors.
Figure 4B:
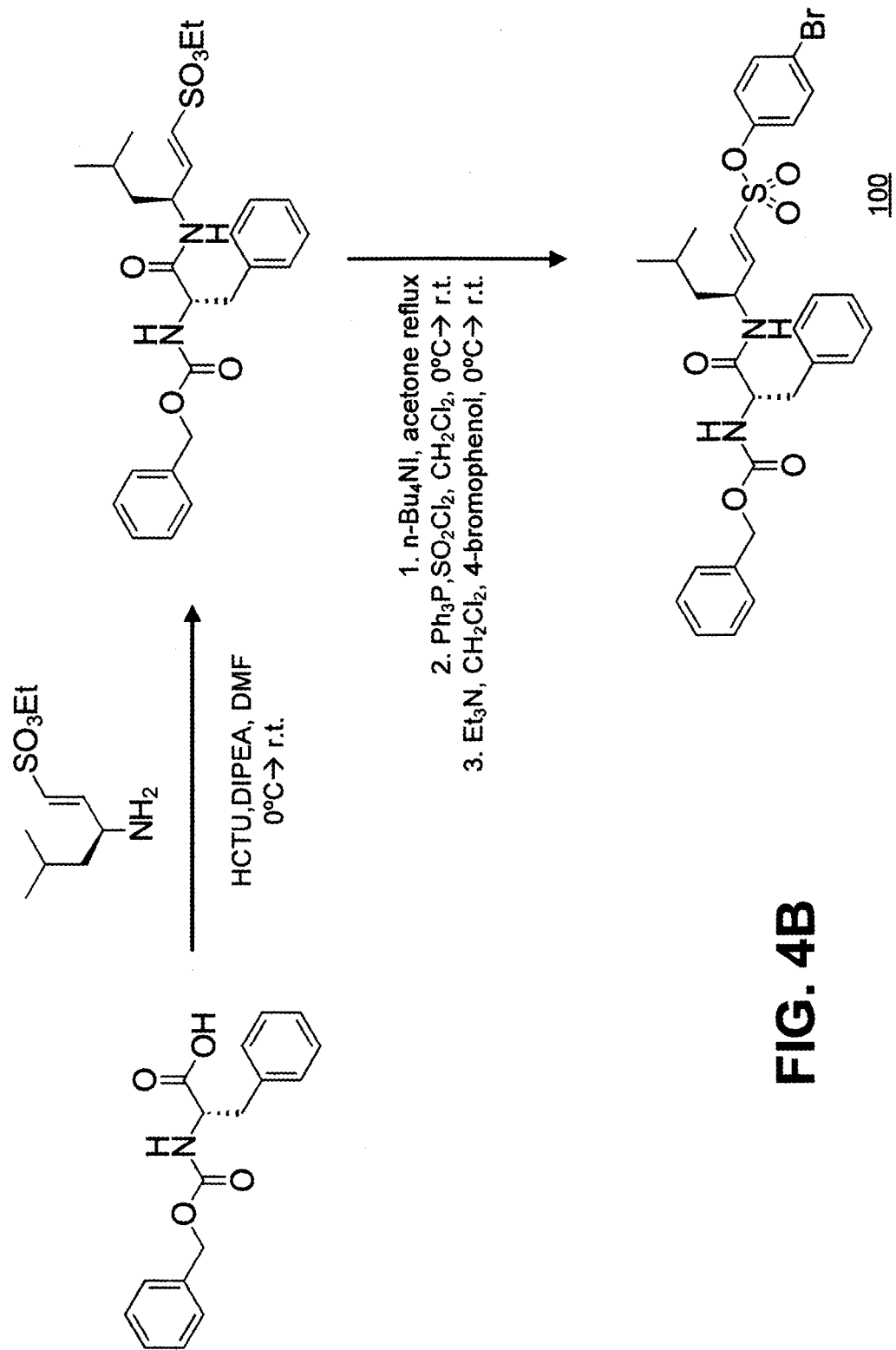
FIG. 4B is a synthetic scheme for using the vinyl sulfonate intermediate to construct cathepsin L inhibitors.
Figure 5:
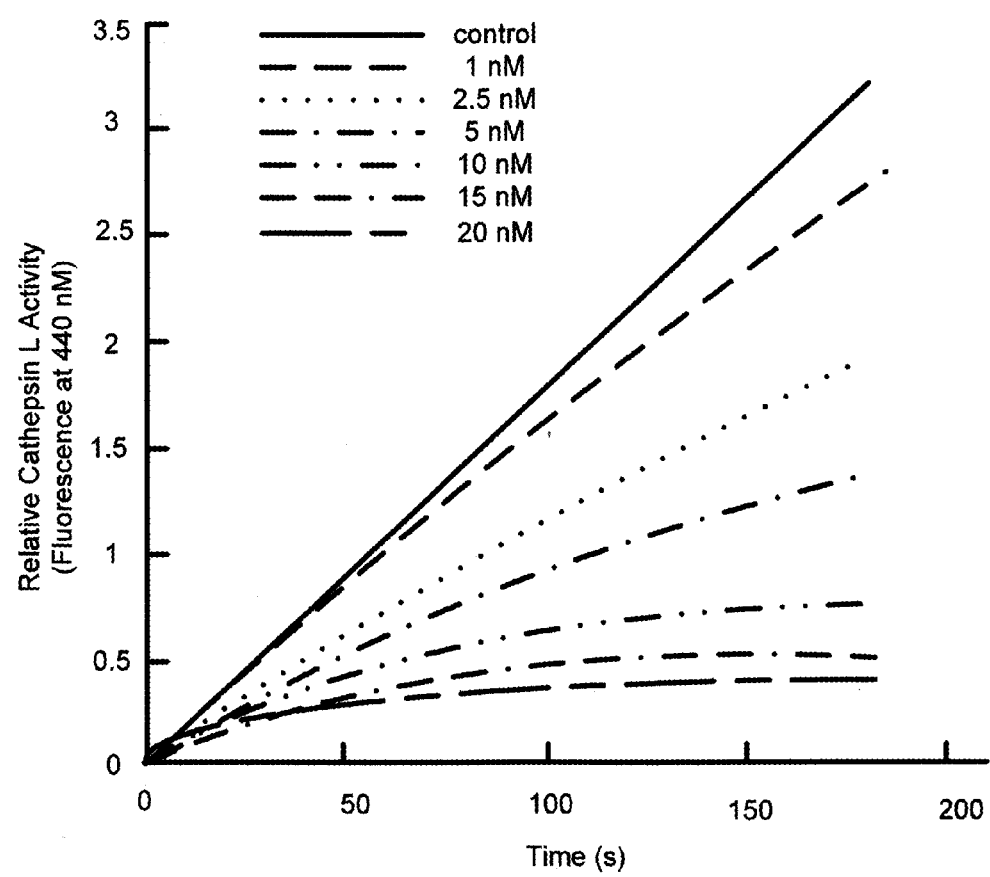
FIG. 5 is a graph depicting cathepsin L-catalyzed hydrolysis of a fluorescent substrate with various concentrations of a cathepsin L inhibitor.

Based on this initial inhibitory screen compound 100 (FIG. 1), was proposed and successfully synthesized from precursor 301 using a multi-step synthetic methodology (FIG. 4A and FIG. 4B). Compound 100 was found to be a potent inhibitor of human cathepsin L ($IC_{50}$ 3.6±0.1 nM). When assayed for activity against active recombinant human cathepsin L, compound 100 displayed a remarkably potent time-dependent and dose-dependent inhibition pattern (see FIG. 5). FIG. 5 depicts a progress curve for cathepsin L-catalyzed hydrolysis of fluorescent substrate, Z-Phe-Arg-(7-Amino-4-methylcoumarin) with various concentration of compound 100. Near complete loss of cathepsin L activity was observed in the presence of 15 nM compound 100 in less than 100 s. The dose-dependent progress curves were utilized to obtain the second order cathepsin L inactivation rate constant ($k_{inact}$). A near diffusion-controlled enzyme inactivation rate was observed (Table 1; $k_{inact}$=4.3×10$^6$ M$^{-1}$ s$^{-1}$) which was consistent with the hypothesis that a hybrid design of ligand would offer considerable advantage in terms of potency and selectivity that would be desired for the development of cathepsin L inhibitor or probe. The mode of inhibition was irreversible because no significant recovery of enzyme activity could be achieved, even after a very large dilution of inactivated reaction mixture.

Another desirable feature for development of a cathepsin L inhibitor or probe is that the inhibitor is highly selective. To demonstrate selectivity, a panel of recombinant proteases and phosphatases were evaluated for their inhibition using steady-state inhibition assays. This panel of enzymes included cysteine cathepsins, an aspartyl cathepsin, a serine cathepsin, a cysteine containing enzyme PTP, and a serine protease. The second order inactivation rate constants were thus determined by performing inactivation kinetics under a pseudo-first order condition (Table 1). In the panel of enzymes tested, compound 100 displayed remarkable selectivity towards cathepsin L. While a 13- and 100-fold selectivity was observed against closest homologous cysteine cathepsins S and K respectively, a very high selectivity (44,000 fold) was observed against cathepsin B. Because many metastatic cancer cells overexpress both cathepsin L and cathepsin B to promote invasion, the disclosed inhibitors and probes are highly effective in delineating the invasive role of cathepsin L alone in these cell types. Furthermore, no reactivity was observed against other panel of enzymes (e.g. aspartyl cathepsin D, serine cathepsin G, and a low pKa cysteine containing enzyme hPTP1B, and serine protease trypsin). A remarkable selectivity profile observed for compound 100 in these experiments is noteworthy, and thus is thought to lend itself well for the development of cathepsin L probes.

TABLE 1

| Enzyme Family | Enzyme | $k_{inact}$ (M$^{-1}$s$^{-1}$) | RSF |
|---|---|---|---|
| Cysteine Cathepsins | Cathepsin L | $4.3 \times 10^8$ | 1 |
| Cysteine Cathepsins | Cathepsin K | $4.4 \times 10^4$ | 100 |
| Cysteine Cathepsins | Cathepsin B | 96 | 44,000 |
| Cysteine Cathepsins | Cathepsin S | $3.4 \times 10^5$ | 13 |
| Cysteine Cathepsins | Cathepsin H | NI* | NA** |
| Cysteine Cathepsins | Cathepsin D | NI* | NA** |
| Cysteine Cathepsins | Cathepsin G | NI* | NA** |
| Protein Tyrosine Phosphatase | hPTP1B | NI* | NA** |
| Serine Protease | Trypsin | NI* | NA** |

Table 1 depicts second order enzyme inactivation rate constants ($k_{inact}$) of compound 100 against a panel of closely-related enzymes. Relative Selectivity Factor (RSF) =$k_{inact}$ (Cathepsin L)/$k_{inact}$ (other enzyme); NI*=no inhibition at 0.1 mM of compound 100 in 1 h, NA**=Not Applicable.

Cell-specific and tissue-specific microenvironments are highly dynamic, and can have a dramatic impact on enzymatic activities and their in vivo function. A direct quantitative reporter of cathepsin L activity in living cancer cells is more desirable for dissecting its role in promoting metastatic cancer. Thus an activity-dependent small molecule probe with desirable cell permeability is urgently needed. To demonstrate that the disclosed cathepsin L inhibitors are cell permeable and therefore suitable for development as an effective probe, an experiment was performed involving metastatic breast cancer MDA-MB-231 cell line. This cell line is known to overexpress cathepsin L, thereby promoting invasion. A commercial cell-permeable fluorescent substrate of cathepsin L (Enzo LifeSciences, Inc.) was utilized to assess the intracellular inhibitory efficacy of compound 100. A near complete loss of intracellular substrate turnover (as indicated by loss of green fluorescence) was evident in cells treated with compound 100, compared to control. This experiment demonstrated that compound 100 was indeed cell permeable and hence suitable for development of an effective cathepsin L probe. Compound 100 is (i) highly potent and selective, (ii) non-basic, (iii) hydrolytically stable, and (iv) cell permeable.

Specifically, the effect of cathepsin L inhibitor 100 on intracellular cathepsin L activity in metastatic breast cancer MDA-MB-231 cell line was examined by fluorescence. Control cells and cells exposed to compound 100 were incubated with (a) vehicle (DMSO 0.05%). The non-control cells were also incubated with compound 100 (750 nM) overnight (22 h). Intracellular inhibition of cathepsin L activity was assessed by exposing the cell to the cell permeable substrate, Z-Phe-Arg-(7-amino-4-methylcomnarin (2 min)). Bright-field, fluorescence and merged images were obtained. A significant loss of green fluorescent signal intensity that emerges from the enzymatic turnover of the fluorescent substrate (white arrow) was observed when compound 100 was present. This experiment demonstrated that compound 100 is a cell permeable inhibitor of cathepsin L activity. The results are representative of three independent experiments. The effectiveness of cathepsin L inhibitor 100 was also evaluated using a functional wound-healing assay (FIG. 6A to 6F).

FIG. 6A to 6F illustrate compound 100 reducing cell migratory potential of highly metastatic MDA-MB-231 breast cancer cells, as assessed by wound healing assays. MDA-MB-231 cells were grown in an eight-well glass dish overnight before treating with DMSO (control, 0.05%, FIGS. 6A, 6B and 6C), and compound 100 (750 nM, FIGS. 6D, 6E and 6F). After creating the wounds, images were taken at three different time intervals: t=0 hr (FIG. 6A and FIG. 6D), 7 hrs (FIG. 6B and FIG. 6E), and 22 hrs (FIG. 6C and FIG. 6F). Representative images of three independent experiments are shown. The dotted lines indicate the edge of the wound at time zero, and the arrows indicate the area of wound closure.

Figure 7:
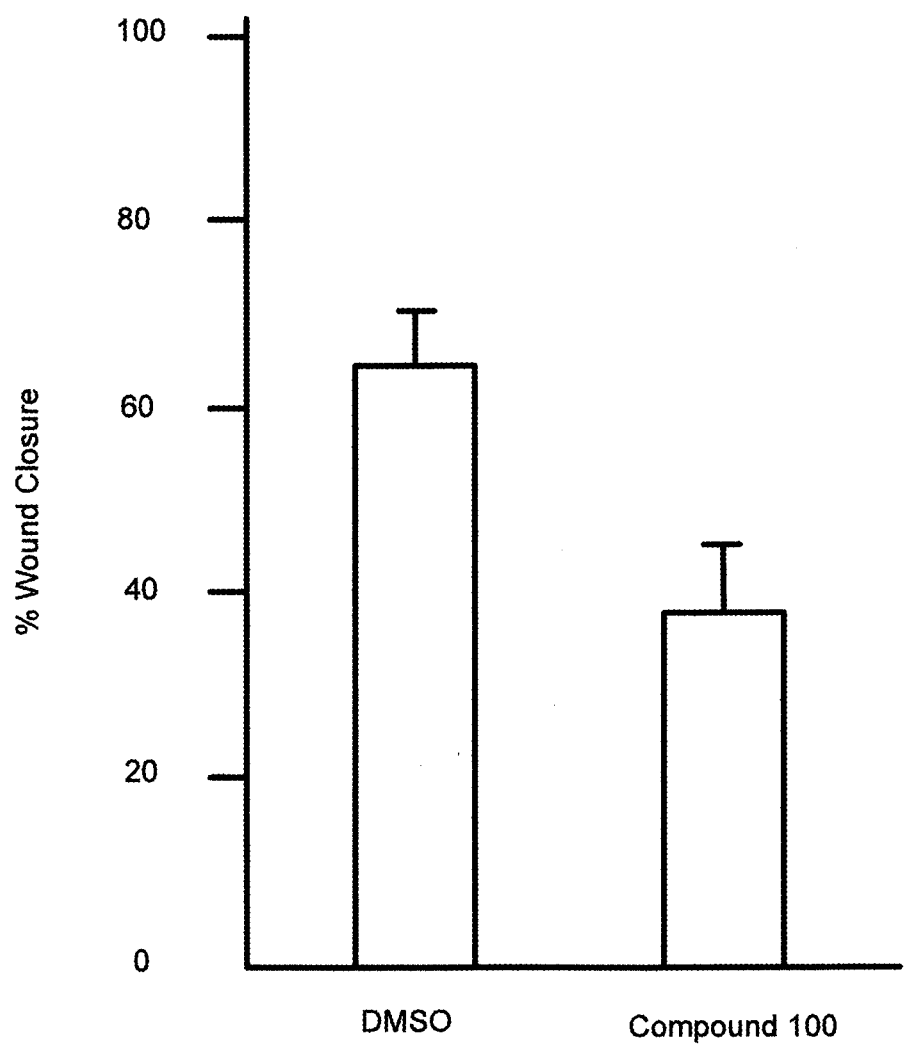
FIG. 7 is a graph showing percent wound closure for a wound exposed to a cathepsin L inhibitor relative to a control.

FIG. 7 depicts wound closure, a direct measure of cell migratory potential, as calculated using the following equation:

% Wound Closure=$[(A_{t=0h}-A_{t=22h})/A_{t=0h}]\times 100\%$, where $A_{t=0h}$ is the area of the wound measured immediately after the scratch, and $A_{t=22h}$ is the area of the wound after 22 hrs. The figure represents a statistical analysis by three independent experiments using the unpaired Student's t test. The data were evaluated as the mean±1 standard deviation. The image analysis were performed by ImageJ software.

An analog of compound 100 was also developed that is intended for use as an activity-based probe. This can be utilized for monitoring cathepsin L activity, and for assessing therapeutic efficacy of cathepsin-targeted drug candidates. The first analog was compound 200 (see FIG. 2) which comprised a small acetylene tag incorporated onto compound 100 without significantly altering its inhibitory efficacy. Because S3 pocket can accommodate a variety of bulky groups, a labeling moiety at this position was believed to be viable. This labeling group may be utilized for performing click chemistry for quantification of active cathepsin L labeling in intact cells. Post-labeling detection using click chemistry was chosen because it offers a wide applicability in biological system. This is primarily because chemistry employed is simple to use, versatile, and is insensitive to oxygen and water. In other embodiments, the labeling moiety is present on another position. In other embodiments, the labeling moiety is an azide.

Figure 8:
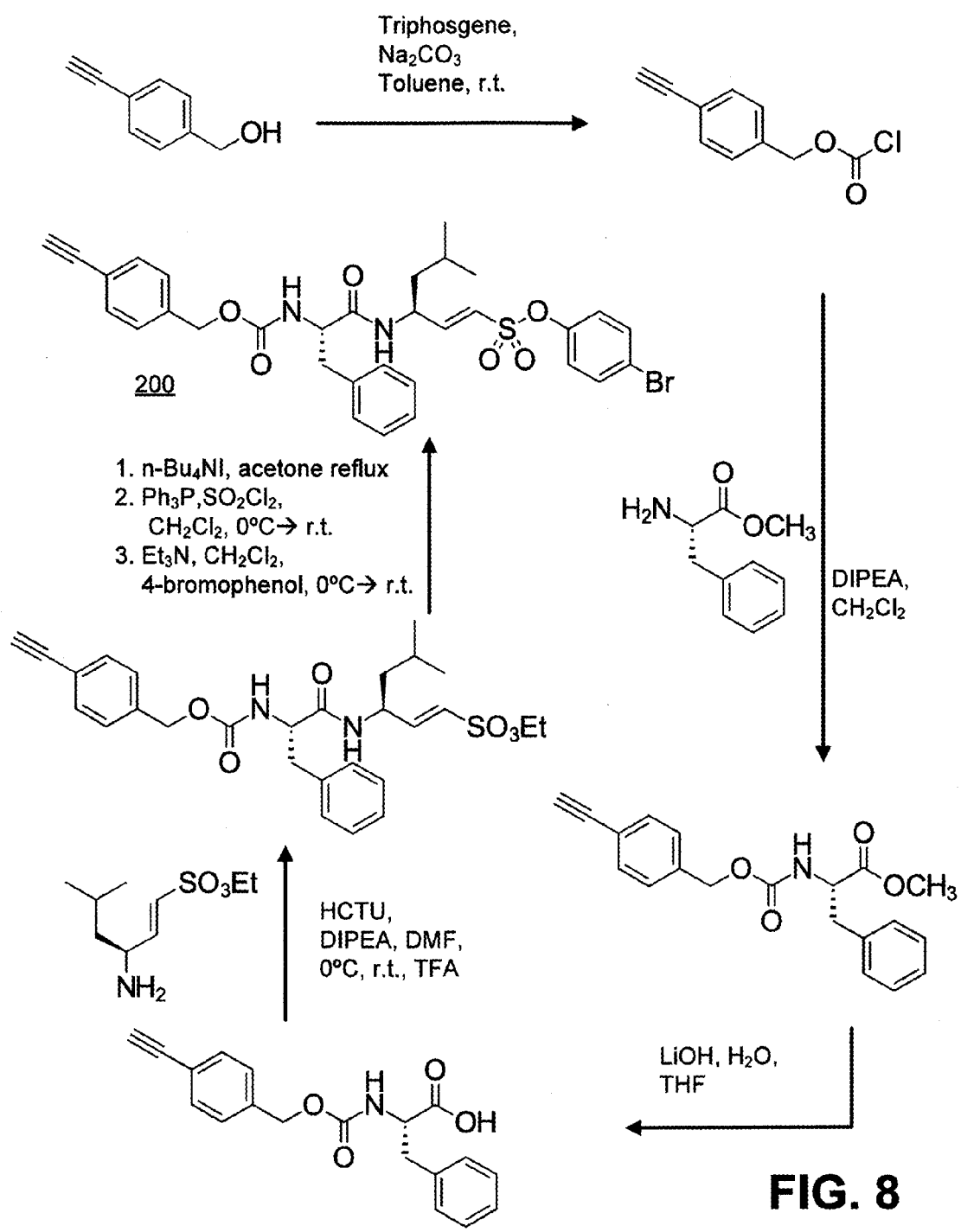
FIG. 8 is a synthetic scheme for preparing a cathepsin L probe.
Figure 9:
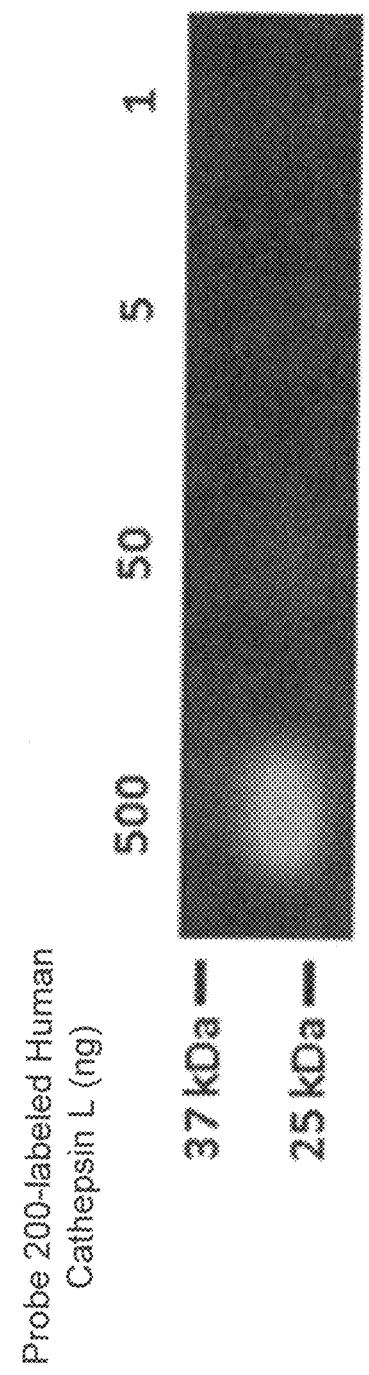
FIG. 9 depicts the results of a gel electrophoresis experiment showing successful labeling of cathepsin L using the probe.

FIG. 8 depicts an exemplary scheme for the synthesis of compound 200. To demonstrate compound 200 can label active human cathepsin L, purified human liver cathepsin L(CatL) was purchased from a commercial source (Enzo Life Sciences). A preliminary experiment was thus setup in the following way. CatL (0.5-500 ng) was activated in 13.5 µL of 50 mM NaOAc buffer (pH 5.5), containing 4 mM DTT) for 30 min. in a 30° C. water bath. 5 mM compound 200 was added to CatL (0.5-500 ng) and the reaction mixture was incubated at 30° C. for 2.5 hours. The resulting reaction mixture was next subjected to standard click chemistry protocol by adding freshly prepared TAMRA solution (4 µl). The TAMRA solution (10 µl) was prepared by mixing 2 µL of 5 mM TAMRA-Azide, 1 µL of 20 mM sodium ascorbate, 4 µL of 10 mM CuSO4, 1 µL of 10 mM THPTA, and 2 µL LC-MS grade water. The resulting sample mixtures were incubated at 30° C. for 12 hours. Following incubation, samples were immediately quenched with Laemmli sample buffer (4×). The sample containing different amount of labeled cathepsin L was loaded in 10% polyacrylamide gel and the protein was resolved. The amount of labeled human cathepsin L was assessed by directly scanning the gel on Typhoon 9410 scanner (Excitation: 532 nm, Emission: 580 nm) (See FIG. 9). As low as 1 ng (about 40 femtomole) of active cathepsin L was detectable using the compound 200 probe.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

20. The composition of matter as recited in claim 19, wherein $R_1$ is Br, n is 0, m is 0, $R_4$ is H, $R_5$ is isopropyl and $R_6$ is phenyl such that Formula (A) is:
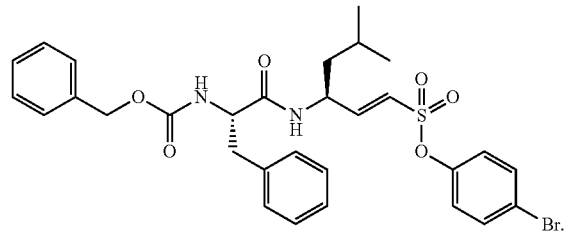 [SMILES: CC(C)C[C@@H](/C=C/S(=O)(=O)Oc1ccc(Br)cc1)NC(=O)[C@H](Cc1ccccc1)NC(=O)OCc1ccccc1]

What is claimed is:

1. A method for inhibiting cathepsin L or probing the activity of cathepsin L, the method comprising steps of:
exposing a biological cell to a compound of Formula (A) or a pharmaceutically acceptable solvate, hydrate, salt or N-oxide thereof:

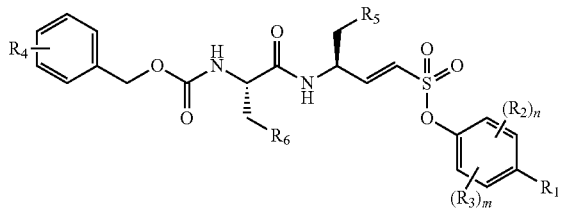

Formula (A)

wherein,
$R_1$ is selected from the group consisting of Br, Cl, I, an aryl, $CO_2CH_3$, CN and $NO_2$;
each $R_2$ is independently selected from the group consisting of F, $CF_3$, aryl and methyl;
each $R_3$ is independently selected from the group consisting of F, $CF_3$ aryl and methyl;
$R_4$ is selected from the group consisting of H, CCH and $N_3$;
$R_5$ is selected from the group consisting of methyl, ethyl and propyl;
$R_6$ is an aryl;
n is 0, 1 or 2
m is 0, 1 or 2.

2. The method as recited in claim 1, where $R_1$ is an aryl group selected from the group consisting of phenyl and p-nitrophenyl.

3. The method as recited in claim 1, wherein $R_1$ is $NO_2$, n is 0, m is 0, $R_4$ is H, $R_5$ is isopropyl and $R_6$ is phenyl.

4. The method as recited in claim 1, wherein $R_1$ is CN, n is 0, m is 0, $R_4$ is H, $R_5$ is isopropyl and $R_6$ is phenyl.

5. The method as recited in claim 1, wherein $R_1$ is phenyl, n is 0, m is 0, $R_4$ is H, $R_5$ is isopropyl and $R_6$ is phenyl.

6. The method as recited in claim 1, wherein $R_1$ is $CO_2CH_3$, n is 0, m is 0, $R_4$ is H, $R_5$ is isopropyl and $R_6$ is phenyl.

7. The method as recited in claim 1, wherein $R_1$ is I, n is 0, m is 0, $R_4$ is H, $R_5$ is isopropyl and $R_6$ is phenyl.

8. The method as recited in claim 1, wherein $R_1$ is Cl, n is 0, m is 1, $R_3$ is methyl, $R_4$ is H, $R_5$ is isopropyl and $R_6$ is phenyl.

9. The method as recited in claim 1, wherein $R_1$ is Cl, n is 2, $R_2$ is F, m is 2, $R_3$ is F, $R_4$ is H, $R_5$ is isopropyl and $R_6$ is phenyl.

10. The method as recited in claim 1, wherein $R_4$ is H, $R_5$ is isopropyl; and $R_6$ is phenyl.

11. The method as recited in claim 1, wherein $R_4$ is CCH or $N_3$, $R_5$ is isopropyl; and $R_6$ is phenyl.

12. The method as recited in claim 1, wherein $R_1$ is Br, n is 0, m is 0, $R_4$ is H, $R_5$ is isopropyl and $R_6$ is phenyl such that Formula (A) is:

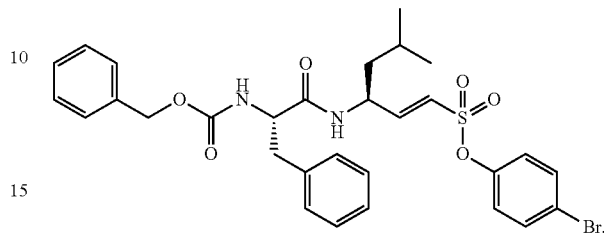

13. The method as recited in claim 1, wherein $R_5$ is isopropyl and $R_6$ is phenyl.

14. The method as recited in claim 13, wherein n is 0 and m is 0.

15. The method as recited in claim 14, wherein $R_1$ is selected from the group consisting of Br, I, phenyl, $CO_2CH_3$, CN and $NO_2$.

16. The method as recited in claim 15, wherein $R_4$ is H.

17. The method as recited in claim 15, wherein $R_4$ is selected from the group consisting of CCH and $N_3$.

18. The method as recited in claim 1, wherein $R_2$ is an aryl selected from the group consisting of NHPh and OPh.

19. A composition of matter with a structure given by Formula (A) or a pharmaceutically acceptable solvate, hydrate, salt or N-oxide thereof

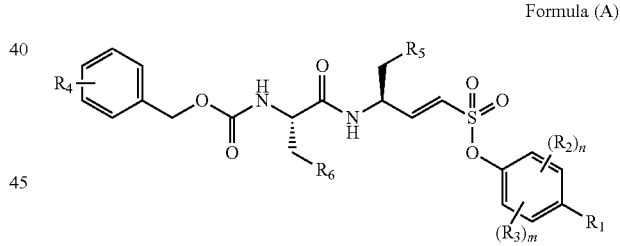

Formula (A)

wherein,
$R_1$ is selected from the group consisting of Br, Cl, I, an aryl, $CO_2CH_3$, CN and $NO_2$;
each $R_2$ is independently selected from the group consisting of F, $CF_3$, aryl and methyl;
each $R_3$ is independently selected from the group consisting of F, $CF_3$ aryl and methyl;
$R_4$ is selected from the group consisting of H, CCH and $N_3$;
$R_5$ is selected from the group consisting of methyl, ethyl and propyl;
$R_6$ is an aryl;
n is 0, 1 or 2
m is 0, 1 or 2.